United States Patent
Mu et al.

(10) Patent No.: US 7,769,059 B2
(45) Date of Patent: *Aug. 3, 2010

(54) HIGH POWER Q-SWITCHED LASER FOR SOFT TISSUE ABLATION

(75) Inventors: Liyue Mu, Fremont, CA (US); Ming Lai, Rochester, NY (US); Kangze Cai, Fremont, CA (US); Weiguo Luo, Fremont, CA (US); Libo Zeng, Saratoga, CA (US)

(73) Assignee: Applied Harmonics Corporation, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/962,823

(22) Filed: Dec. 21, 2007

(65) Prior Publication Data

US 2008/0095201 A1 Apr. 24, 2008

Related U.S. Application Data

(63) Continuation of application No. 11/056,671, filed on Feb. 12, 2005, now Pat. No. 7,313,155.

(60) Provisional application No. 60/544,034, filed on Feb. 12, 2004.

(51) Int. Cl.
*H01S 3/11* (2006.01)
(52) U.S. Cl. .............................. 372/10; 372/11; 372/17
(58) Field of Classification Search ............ 372/10, 372/11
See application file for complete search history.

(56) References Cited

U.S. PATENT DOCUMENTS

| | | | |
|---|---|---|---|
| 4,675,872 A | 6/1987 | Popek et al. | 372/10 |
| 5,066,291 A | 11/1991 | Stewart | 606/3 |
| 5,151,909 A * | 9/1992 | Davenport et al. | 372/22 |
| 5,312,396 A | 5/1994 | Feld et al. | 606/11 |
| 5,776,175 A | 7/1998 | Eckhouse et al. | 607/100 |

(Continued)

OTHER PUBLICATIONS

Malek et al., "High-Power Potassium-Titanyl-Phosphate (KTP/532) Laser Vaporization Prostatectomy: 24 Hours Later", *Urology*, vol. 51, 1998, Elsevier Science Inc., pp. 254-256.

(Continued)

*Primary Examiner*—Dung T Nguyen
(74) *Attorney, Agent, or Firm*—Pillsbury Winthrop Shaw Pittman, LLP (57) ABSTRACT

The present invention discloses a high power Q-switched, intracavity frequency-doubled laser for laser ablation of soft tissue. Operating a high power Q-switched laser in a frequent on-off mode is highly desirable for laser prostatectomy. Giant first pulse may occur when a Q-switched laser is switched from laser-ready mode to pulse-on mode due to sudden depletion of stored energy in the gain medium. Such a giant first pulse may cause power damage of intracavity optics. Besides, temperature shock induced by sudden onset of a high power pulse train may cause optical damage on surface coating of intracavity optics. The present invention contemplates to suppress these giant first pulses and temperature shocks through pre-lasing and ramping profile of laser parameters. Reliable and frequent on-off operation of a diode-pumped, Q-switched, frequency-doubled Nd:YAG laser is demonstrated for output power up to 100 W.

16 Claims, 5 Drawing Sheets

U.S. PATENT DOCUMENTS

| | | | | |
|---|---|---|---|---|
| 5,805,622 | A | | 9/1998 | Brinkmann .................... 372/9 |
| 6,009,110 | A | * | 12/1999 | Wiechmann et al. .......... 372/10 |
| 6,031,854 | A | | 2/2000 | Ming .......................... 372/22 |
| 6,038,241 | A | * | 3/2000 | von Elm et al. ............... 372/30 |
| 6,309,352 | B1 | | 10/2001 | Oraevsky et al. ............ 600/407 |
| 6,413,267 | B1 | | 7/2002 | Dumoulin-White et al. ... 607/89 |
| 6,554,824 | B2 | | 4/2003 | Davenport et al. ............. 606/3 |
| 6,723,090 | B2 | | 4/2004 | Altshuler et al. ............... 606/9 |
| 6,986,764 | B2 | | 1/2006 | Davenport et al. ............. 606/3 |
| 7,313,155 | B1 | * | 12/2007 | Mu et al. ....................... 372/10 |
| 2001/0031960 | A1 | | 10/2001 | Kliewer et al. ................. 606/5 |
| 2003/0058403 | A1 | | 3/2003 | Lai et al. .................... 351/212 |
| 2003/0130649 | A1 | | 7/2003 | Murray et al. ................. 606/3 |
| 2003/0135205 | A1 | | 7/2003 | Davenport et al. ............. 606/3 |
| 2003/0156605 | A1 | | 8/2003 | Richardson et al. .......... 372/25 |
| 2004/0022280 | A1 | | 2/2004 | Lai et al. ....................... 372/5 |
| 2004/0236319 | A1 | | 11/2004 | Davenport et al. ............. 606/3 |
| 2005/0027286 | A1 | | 2/2005 | Davenport et al. ............. 606/3 |
| 2005/0256513 | A1 | | 11/2005 | Murray et al. ................. 606/3 |
| 2005/0288653 | A1 | | 12/2005 | Lai et al. ...................... 606/10 |
| 2006/0007965 | A1 | | 1/2006 | Tankovich et al. ........... 372/10 |

OTHER PUBLICATIONS

Randall S. Kuntzman et al., "High-Power Potassium Titanyl Phosphate Laser Vaporization Prostatectomy", *Mayo Clinic Proc.*, vol. 73, 1998, pp. 798-801.

R. S. Malek et al., "High Power Potassium-Titanyl-Phosphate Laser Vaporization Prostatectomy", *The Journal of Urology*, vol. 163, Jun. 2000, pp. 1730-1733.

Mahmood A. Hai et al., "Photoselective Vaporization of the Prostate: Initial Experience with a New 80 W KTP Laser for the Treatment of Benign Prostatic Hyperplasia", *Journal of Endourology*, vol. 17, No. 2, Mar. 2003, pp. 93-96.

Walter Koechner, "Solid-State Laser Engineering", $5^{th}$ Edition, Springer-Verlag Berlin Heidelerg, New York, 1999, 12 pages.

Anthony E. Siegman, "Lasers", University Science Books, Mill Valley, California, 1986, 26 pages.

"Photoselective Vaporization of the Prostate", *Supplement to Urology Times*, vol. 30, Supplement 1, May 2002, 20 pages.

Randall S. Kuntzman et al., "High-Power (60-Watt) Potassium-Titanyl-Phosphate Laser Vaporization Prostatectomy in Living Canines and in Human and Canine Cadavers", *Urology*, vol. 49, No. 5, 1997, Elsevier Science Inc., pp. 703-708.

Alfred Vogel et al., "Mechanisms of Pulsed Laser Ablation of biological Tissues", *Chem. Rev.*, vol. 103, Published on Web Feb. 12, 2003, pp. 577-644.

Tuan Vo-Dinh, "Biomedical Photonics Handbook", CRC Press, 2003, pp. 2-1 to 2-75, 5-1 to 5-16.

V. V. Golovlyov et al. "Ablation of an Optically Homogeneous Absorbing Medium by Scattered Pulsed Laser Radiation", *Applied Physics B*, vol. 57, 1993, p. 451.

R. O. Esenaliev et al., "Laser Ablation of Aqueous Solutions with Spatially Homogeneous and Heterogeneous Absorption", *Applied Physics B*, vol. 59, 1994, p. 73.

Lawrence Livermore National Lab, "The Short-Pulse Laser: A Safe, Painless Surgical Tool", *Science & Technology Review*, Oct. 1995, 3 pages.

V. Venugopalan et al., "Thermodynamic Response of Soft Biological Tissues to Pulsed Infrared-Laser Irradiation", *Biophysical Journal*, vol. 70, Jun. 1996, pp. 2981-2993.

M. Ogura et al., "Myocardium Tissue Ablation with High-Peak-Power Nanosecond 1.064- and 532-nm Pulsed Lasers: Influence of Laser-Induced Plasma", *Lasers in Surgery and Medicine*, vol. 31, 2002, pp. 136-141.

J. Niamtu, "Clinical Applications of the 532-nm Diode Laser for the Treatment of Facial Telangiectasia and Pigmented Lesions: Literature Review, History, and Discussion of Clinical Experience", *The American Journal of Cosmetic Surgery*, vol. 18, No. 2, 2001, pp. 71-81.

S. Uhlhorn, "Free Electron Laser Ablation of Soft Tissue: The Effects of Chromophore and Pulse Characteristics of Ablation Mechanics", *Ph.D. Dissertation*, Vanderbilt University, Aug. 2002, 113 pages.

A. F. El-Sherif and T. A. King, "Soft and Hard Tissue Ablation with Short-Pulse High Peak Power and Continuous Thulium-Silica Fibre Lasers", *Lasers Med. Sci*, vol. 18, No. 3, 2003, p. 139.

A. Liu et al., 60-W Green Output by Frequency Doubling of a Polarized Yb-Doped Fiber Laser, *Optic Letters*, vol. 30, No. 1, Jan. 1, 2005, pp. 67-69.

F. H. Loesel et al., "Laser-Induced Optical Breakdown on Hard and Soft Tissues and Its Dependence on the Pulse Duration: Experiment and Model", *IEEE Journal of Quantum Electronics*, vol. 32, No. 10, Oct. 1996, pp. 1717-1722.

F. Sengor et al., "A Comparative Study of Laser Ablation and Transurethral Electroresection for Benign Prostatic Hyperplasia: Results of a 6-Month Follow-Up", *British Journal of Urology*, vol. 78, Issue 3, 1996, abstract only.

M. Grasso et al., "Lasers in Urology", http://www.emedicine.com/med/topic3037.htm, Mar. 2006, 15 pages.

J. Berger et al., "370 mW, 1:06 µm, CW $TEM_{00}$ Output from an Nd: YAG Laser Rod End-Pumped by a Monolithic Diode Array", Apr. 13, 1987, *Electronics Letters*, vol. 23, No. 13, Jun. 18, 1987, pp. 669-670.

\* cited by examiner

HIGH POWER Q-SWITCHED LASER FOR SOFT TISSUE ABLATION

CROSS REFERENCE TO RELATED APPLICATIONS

This application is a continuation of U.S. patent application Ser. No. 11/056,671, filed Feb. 12, 2005, now U.S. Pat. No. 7,313,155, entitled "High Power Q-Switched Laser for Soft Tissue Ablation", which claims the benefit of U.S. Provisional Application No. 60/544,034, filed on Feb. 12, 2004, each of which are incorporated herein by reference in their entirety.

FIELD OF THE INVENTION

This invention relates in general to laser ablation with a high power Q-switched solid-state laser and in particular to frequent on-off operation of a high power Q-switched laser for ablating prostate tissue.

DESCRIPTION OF THE PRIOR ART

High power, Q-switched solid-state laser has demonstrated a great potential in laser ablation of prostate tissue. It is desirable in a laser prostate surgery for the surgeon to turn on and off the laser pulses freely and frequently. However, intracavity optics in a high power Q-switched laser is more vulnerable to power damage during the transient of turning to a pulse-on mode.

In a Q-switched solid-state laser, a giant first pulse may be generated when energy stored in laser gain-medium is suddenly depleted at the transient of switching the laser from its laser-ready mode to its pulse-on mode. In a laser-ready mode, population inversion in the gain medium is built up but the laser is held from lasing via high loss of the Q-switch. In a high power solid-state laser, population inversion may reach an extremely high level in laser-ready mode. When the laser is switched to a pulse-on mode, the Q-switch is operated in a sequence of on-off loss modulation to produce a train of laser pulses.

At the onset to pulse-on mode, a first pulse builds up rapidly and energy stored in gain-medium is depleted sharply toward zero. After the first few pulses, population inversion reaches an equilibrium that is typically well below the population inversion in laser-ready mode. If the stored energy is rapidly dumped into a first pulse, this first pulse may have substantially higher laser energy and shorter pulse width. Consequently, this first pulse may have significantly higher peak-power than the subsequent pulses. This phenomenon is undesirable in many applications such as laser prostate surgery. The giant first pulse may damage laser optics as well as laser-delivering fiber and interrupt surgical procedures.

In a high power, frequency-doubled solid-state laser, a nonlinear crystal is typically incorporated for wavelength conversion. This nonlinear crystal is also vulnerable to power damage from giant first pulse. Several prior-art approaches are developed to suppress the otherwise giant first pulse of high power Q-switched laser.

In U.S. Pat. No. 6,554,824, a lamp-pumped Q-switched laser is disclosed for laser treatment of soft tissue, in which the first pulse is suppressed by reducing the pump power prior to the pulse-on mode. With a reduced pump power, stored energy in gain-medium is low prior to laser-on mode. The amplitude of the first pulse is thus suppressed. A limitation of this prior-art approach is that the pump power must be ramped up and down between laser-ready mode and pulse-on mode, which results in a substantial change in heat loading laser crystal and its pump source. Such a change is less favorable for a diode pump source.

In U.S. Pat. No. 6,038,241, precise control of first pulse is implemented into a diode-pumped Q-switched laser. In this prior-art approach, RF power to Q-switch and/or pump power to laser is precisely controlled and modified at the onset of pulse-on mode. The advantage of this prior-art approach is that the first pulse can have the same amplitude as the other pulses in a Q-switched pulse train. A limitation is that its electrical-optical system is very complex and is difficult to be implemented into an intracavity frequency-doubled laser.

In U.S. Pat. No. 6,009,110, first-pulse control is applied to a diode-pumped Q-switched UV laser. Amplitude of first UV pulse is regulated via modifying RF power to Q-switch and controlling population conversion prior to pulse-on mode. The advantage of this prior-art approach is that the first UV pulse can be well controlled for a Q-switched UV laser. A limitation is that prior to pulse-on mode the laser produces high intracavity power of CW infrared laser and thus generates a CW beam of second harmonics, which is not desirable for surgical laser ablation.

SUMMARY OF THE INVENTION

The present invention discloses a new and improved method of first pulse suppression to overcome above identified limitations and contemplates implementing such first pulse suppression into a high power, Q-switched, intracavity frequency-doubled laser. The present invention also contemplates applying such first pulse suppression into a Q-switched surgical laser with output power of 40 W or higher. The present invention further contemplates using such first pulse-suppressed laser for soft tissue ablation that requires frequent switching between laser-ready and pulse-on modes.

In this present invention, a special pre-lasing and ramp-up control is adapted to obtain a ramp-up profile of the pulse train when the laser is switched from its laser-ready mode to pulse-on mode. This ramp-up control can prevent first pulse damage and improve reliability of high power intracavity frequency-doubled laser. It is particular useful for Q-switched surgical laser with average output power over 40 W.

In this present invention, when the laser is switched from laser-ready mode to pulse-on mode, the laser output power is gradually ramped up to a stable power. The first few laser pulses have their amplitudes lower than the consecutive pulses in the train. A ramp up profile of pulse train can be realized by a proper control of Q-switch transmission, which has a minimum and a maximum value. The Q-switch transmission increases when RF power level on the Q-switch decreases. A ramp up profile of pulse train can also be realized by a proper control of Q-switch gate width, which has a typical value of 1 to 10 microseconds. With such a ramp up profile of pulse amplitude, the nonlinear crystal for frequency doubling is heating up gradually and transient temperature gradient inside the crystal and on the crystal surface is thus greatly reduced.

In a first preferred embodiment of the present invention, transmission of the Q-switch is controlled via RF power fed onto the Q-switch. During the laser-ready mode, full RF power is applied continuously and Q-switch transmission is zero, quenching any laser action. Upon receiving a trigger signal to switch the laser into pulse-on mode, the RF power is firstly ramped down to zero such that the laser produces low power, continuous wave output. Population inversion of the gain-medium is thus reduced to a level of CW operation. The RF power is then ramped up to restore population inversion and switched on-off as in a normal Q-switched operation. The ramp-up time used is longer than a few cycles of pulse repetition, and the laser pulses within the ramp-up time have lower pulse energy than the pulses thereafter. The CW pre-lasing prior to ramp-up prevents the formation of a giant first pulse, while the ramp up further reduces temperature shock to intracavity optics.

This first embodiment of the present invention has minimal technical complexity. Controlling RF power ramp-down and ramp-up can be accomplished by modulating a control signal to the RF driver. The control signal can be generated by either digital, digital-analog combination, or analog circuit. In digital format, the ramp-down and ramp-up waveform is pre-programmed and stored in a microprocessor of the laser controller. A fast digital to analog converter converts the digital waveform to analog waveform that is then fed into the RF driver. In digital-analog combination, a pre-programmed digital signal is used to trig a waveform signal generated by an analog RC circuit. In analog method, an analog RC circuit is triggered by external signal that generates a control waveform.

In a second preferred embodiment of the present invention, both Q-switch transmission and laser pump current are modulated to suppress first laser pulses. When the laser is switched to laser-ready mode, the laser pump current is reduced to below normal operation current. Once receiving a trigger signal for next pulse-on mode, the Q-switch driver ramps the RF power down to zero and then sharply turns the RF power to a normal on-off Q-switch operation without a ramping process. Any energy stored inside the gain-medium is damped to CW lasing level during the period that the RF power is ramped down. When RF power reaches to zero, i.e., the Q-switch switches to transparent, the laser pump current ramps up to its normal operation level. The ramp-up time determines the number of pulses to be suppressed. This current ramp-up process is slow such that the wavelength of diode laser (i.e. the pump laser radiation) remains unchanged and diode laser performance is not affected. As a result, the first few pulses have lower amplitude than the consecutive pulses.

In a third preferred embodiment of the present invention, gate signal to the Q-switch is modified at the onset of pulse-on mode to suppress first laser pulses. Upon receiving a trigger signal for pulse-on mode, the Q-switch driver ramps the RF power sown to zero and then turns the RF power to an on-off Q-switch mode with a modified gate signal. Any energy stored inside the gain-medium is damped to CW lasing level while the RF power ramps down. The first few gate pulses to the RF driver have narrower gate width of about 1 to 2 microseconds, in comparison to normal gate width of 4 to 10 microseconds. When the gate width is narrower than pulse buildup time of a Q-switch laser, energy stored inside the gain-medium cannot be completely depleted into a pulse. Combining CW pre-lasing and narrower early gate pulses, first few pulses can be generated with a ramp-up profile in amplitude. The modified gate signal can be generated by digital, digital-analog or analog method. Digital method is usually the simplest.

For soft tissue ablation, a high power Q-switched laser is usually delivered through an optical fiber. A major motivation of the present invention is to prevent optical damage from giant first laser pulses and laser induced temperature shock. The most vulnerable optics subject to this damage is the surface coating of intracavity nonlinear crystal and the tip of laser delivery fiber. Gradually ramping up the amplitude of laser pulses allows more time for laser heating to dissipate and thus minimizes temperature shock on surface coating of nonlinear crystal and fiber tip. The above and other objectives and advantages of the present invention will become more apparent in the following drawings, detailed description, and claims.

BRIEF DESCRIPTION OF THE FIGURES

FIG. 3a) external trigger signal ET, 3b) gate signal GS, 3c) first pulse control signal FPC, 3d) RF power RFP and 3e) laser pulse LP.

FIG. 4a) external trigger signal ET, 4b) gate signal GS, 4c) first pulse control signal FPC, 4d) RF power RFP, 4e) pump current C and 4f) laser pulse LP.

FIG. 5a) external trigger signal ET, 5b) gate signal GS, 5c) first pulse control signal FPC, 5d) RF power RFP, and 5e) laser pulse LP.

DETAILED DESCRIPTION OF THE FIGURES

Figure 1:
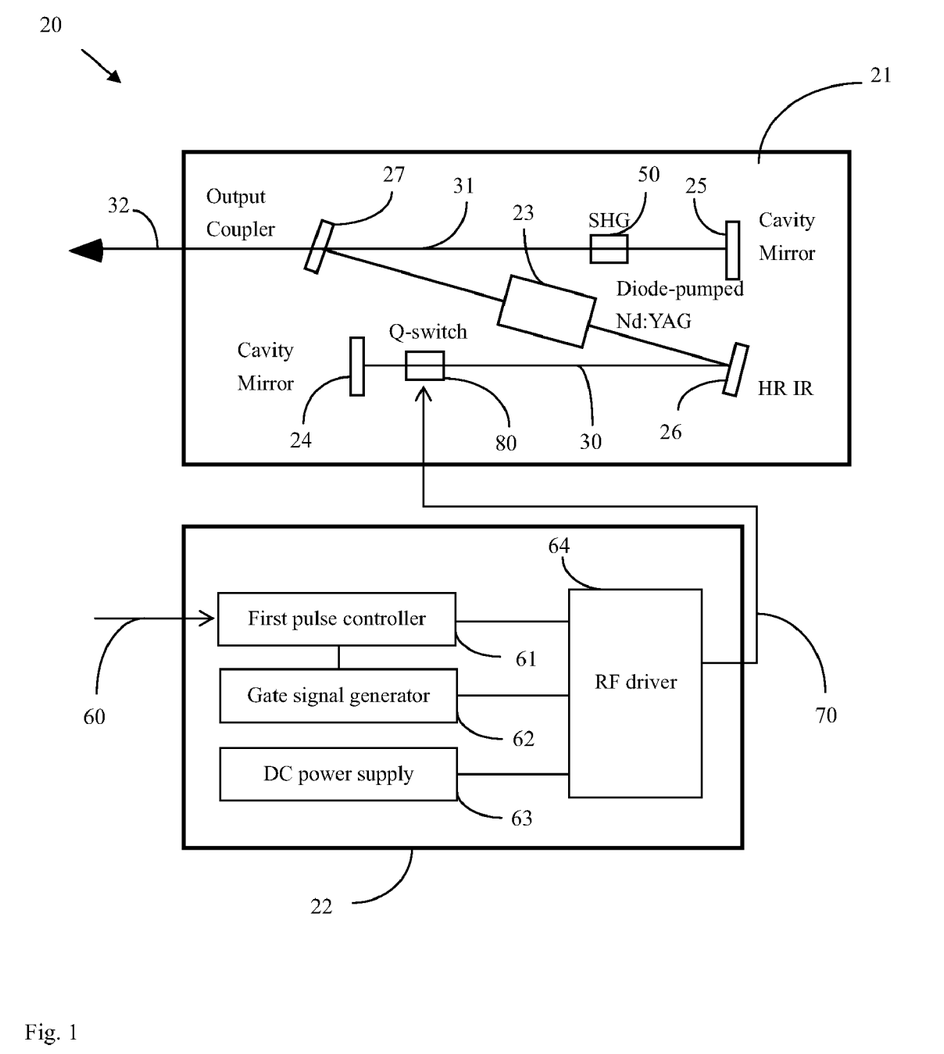
FIG. 1 is a schematic diagram showing a high power Q-switched, intracavity frequency-doubled laser.

FIG. 1 is a schematic diagram showing a high power Q-switched, intracavity frequency-doubled laser system 20, in accordance with the present invention. The laser system 20 includes a laser head 21 and a RF controller 22, while power supply of the laser is not shown in the drawing. The laser head 21 consists of a pump-head 23, a Q-switch 80, a second harmonic generator 50 and an oscillator cavity formed with reflectors 24, 25, 26, and 27.

The laser head 21 houses pump source of diode lasers and a gain medium of Nd:YAG rod. The infrared cavity mirror 24 has dielectric coating for high reflection HR at 1064 nm. The infrared/visible cavity mirror 25 has coating for HR at 1064 nm/532 nm. The infrared folding mirror 26 has coating for HR at 1064 nm, and the output coupler 27 has dielectric coating for HR at 1064 nm and high transmission HT at 532 nm. An acoustic-optical Q-switch 80 is located near the cavity mirror 24. A second harmonic generator SHG 50 is placed near the other cavity mirror 25. Both surfaces of SHG 50 have anti-reflection coatings for both infrared (1064 nm) and visible (532 nm) wavelength. The SHG 50 converts fundamental light at 1064 nm into second harmonic light at 532 nm. In laser cavity, infrared beam path 30 is from cavity mirror 24 to cavity mirror 25, while visible beam path 31 is from cavity mirror 25 to output coupler 27. Depending on output coupler 27, the output beam 32 can have either dual-wavelength (532 nm and 1064 nm) or single wavelength (532 nm).

In this present invention, preferred SHG 50 crystal is LBO, which can be cut for either type I phase-matching or type II phase-matching. The SHG 50 is usually temperature regulated with a temperature controller. For a given LBO crystal of SHG 50, conversion efficiency depends on infrared laser power density inside the SHG 50 and phase matching conditions. In general, the higher the power density is, the higher the conversion efficiency is. The damage threshold of a particular SHG 50 crystal depends on surface polish quality, anti-reflection coating quality, laser beam profile and temperature gradient on crystal surfaces. Maximum power density on SHG 50 is usually limited by anti-reflection coatings, of which a damage threshold is typically a few tens of megawatts per square centimeter for laser pulses with kHz repetition rate. The laser head 21 is designed and built upon a balance between high conversion efficiency and safe operation for high power second harmonic generation.

RF controller 22 is an electronics device providing Q-switch 80 with modulated RF power. The RF controller 22 consists of a first pulse controller 61, a gate signal generator 62, a DC power supply 63 and an RF driver 64. Once receiving an external signal 60, the first pulse controller 61 processes the signal 60 according to a predetermined algorism and sends a first pulse controlling signal to RF driver 64 and a trigger signal to gate signal generator 62. The gate signal generator 62 then generates TTL pulses with predetermined pulse width and pulse repetition rate. Typically the pulse width is 4 to 10 microseconds and the pulse repetition rate is in kilo-Hz range. The DC power supply 63 powers the RF driver 64, which generates RF power with a fixed RF frequency (e.g. 24 MHz or 27 MHz). RF power for Q-switch ranges typically from few watts to few tens of watts. The signal from first pulse controller 61 modulates the gate signal generator 62, which in turns modulates the RF driver 64. The final modulated RF power, which can control the first pulse amplitude and provide regular Q-switched pulses, is sent to Q-switch 80 via RF cable 70.

Figure 2:
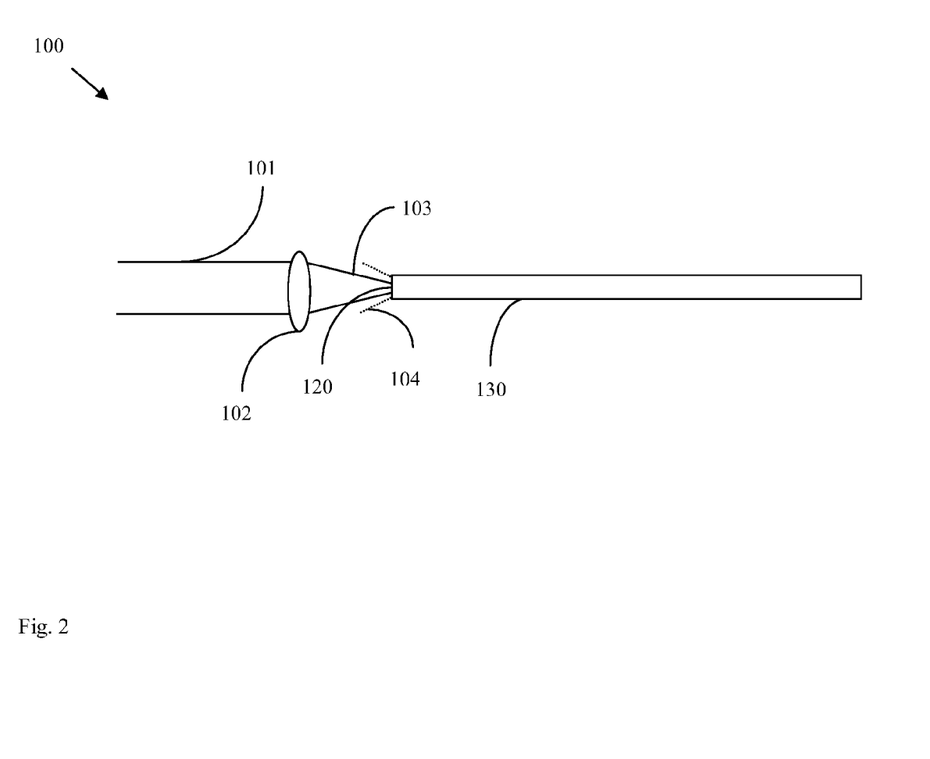
FIG. 2 shows coupling a laser beam into an optical fiber.

FIG. 2 shows a diagram 100 coupling a laser beam into an optical fiber. Laser beam 101 is tightly focused with a lens 102 onto a fiber surface 120. For soft tissue ablation, fiber 130 is a multimode fiber made of, for instance, fused silica. To achieve optimal coupling efficiency, numeric aperture 103 of the lens 102 is smaller than the numeric aperture 104 of fiber 130.

Figure 3:
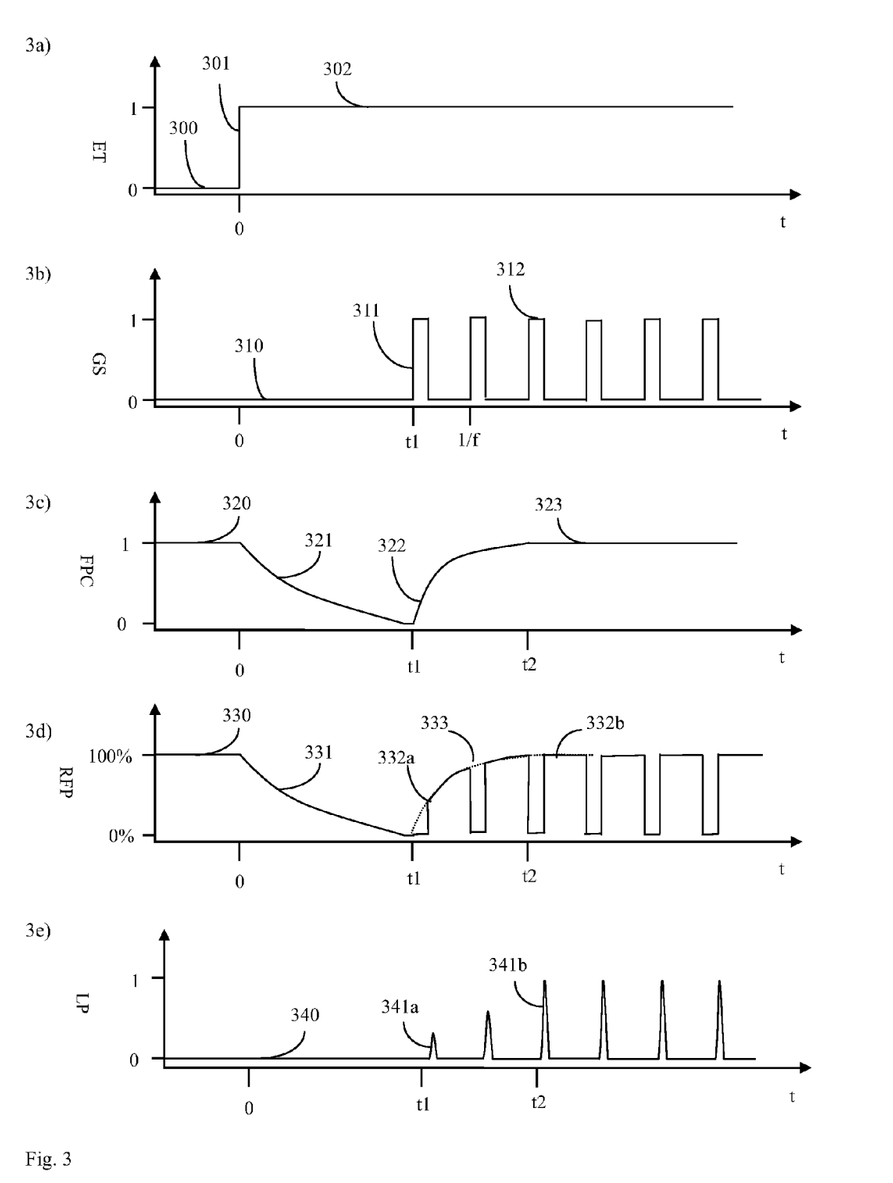
FIG. 3 illustrates schematically first pulse suppression through pre-lasing and FR power ramping.
Figure 4:
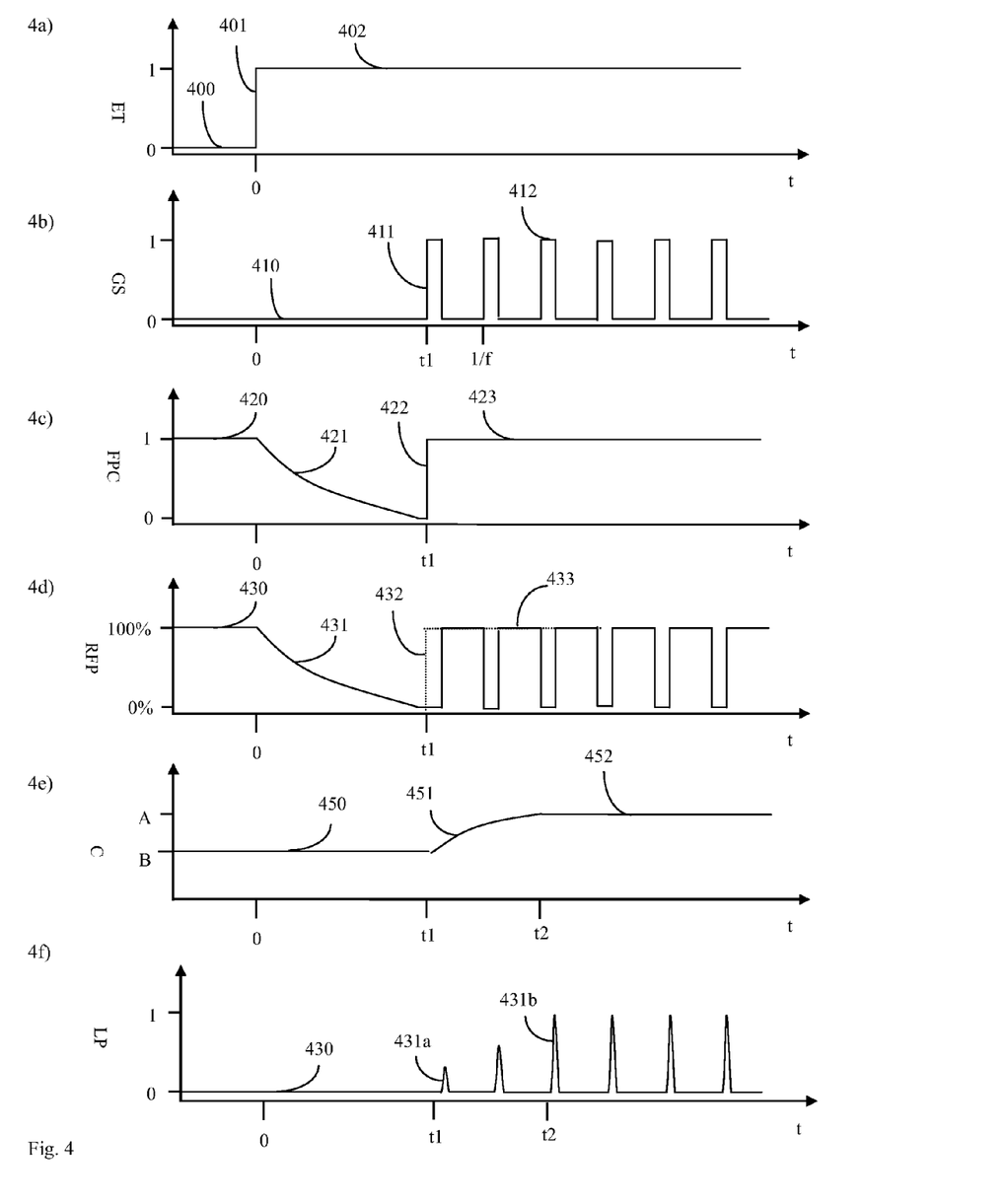
FIG. 4 illustrates schematically first pulse suppression through pre-lasing and pump current ramping.
Figure 5:
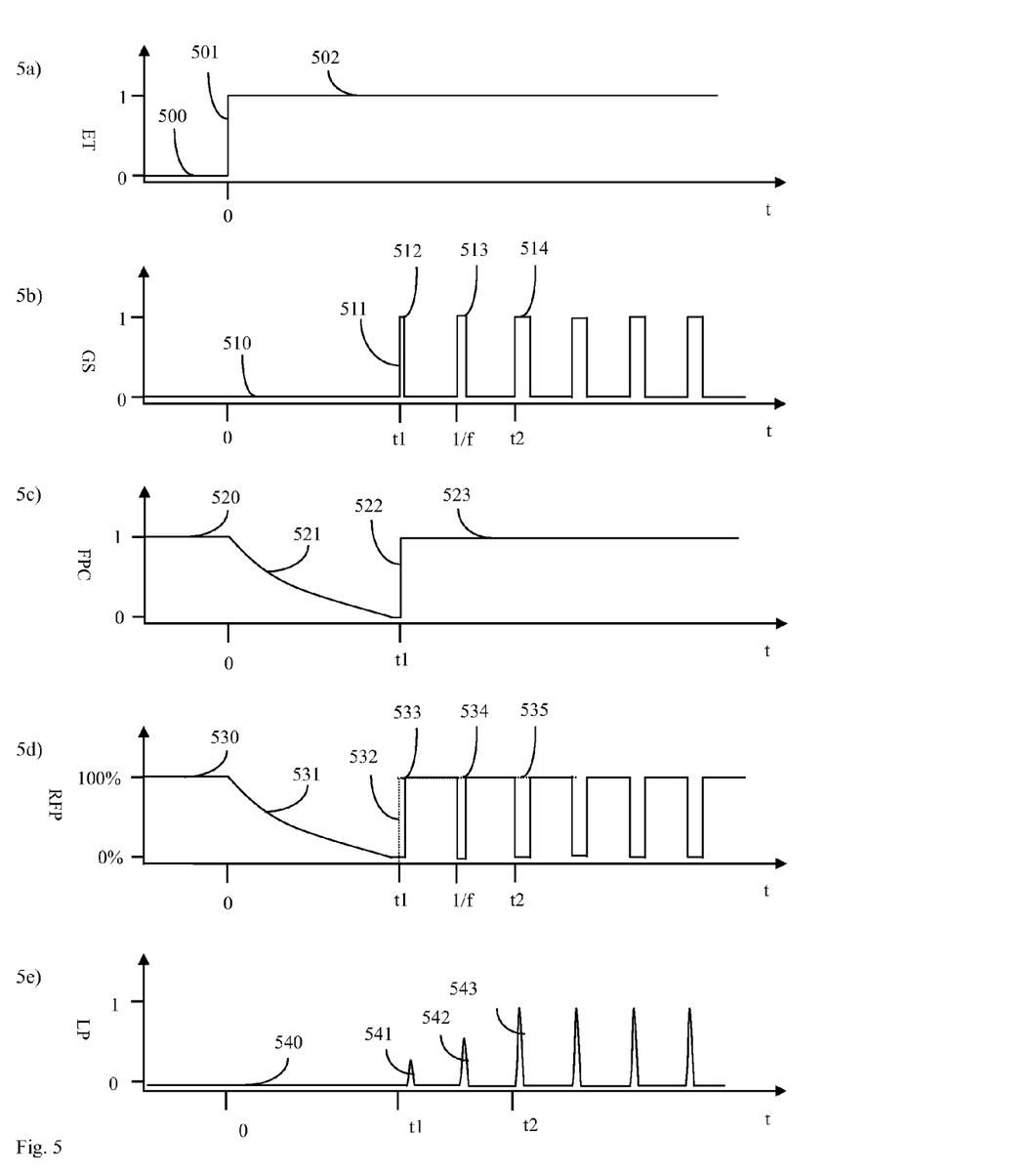
FIG. 5 illustrates schematically first pulse suppression through pre-lasing and gate width ramping.

FIG. 3 through FIG. 5 illustrate schematically first pulse suppression in various embodiments in accordance with the present invention. FIG. 3 illustrates schematically first pulse suppression through pre-lasing and FR power ramping. FIG. 3a) shows temporal profile of external trigger signal ET, 3b) gate signal GS, 3c) first pulse control signal FPC, 3d) RF power RFP and 3e) laser pulse LP. Here the diode pump current C (not shown) is kept constant. During previous laser-ready mode, the ET 300 equals to 0, GS 310 equals to 0, FPC 320 equals to 1, RFP 330 equals to 100% and LP 340 equals to 0. LP 340 equals to 0 indicating no laser pulse output.

At time 0 laser is switched from laser-ready mode to pulse-on mode, the input signal ET 301 of the first pulse controller 61 changes from 0 to 1. As a response, the first pulse controller 61 sends a ramp-down signal 321 to RF driver 64 and sends a delayed signal at time t1 to the gate signal generator 62 that starts a gate signal 311. The RFP 331 to Q-switch 80 follows the ramp-down curve of FPC 321. The purpose of this ramp-down process is to deplete energy stored inside medium during the laser-ready mode. The LP 340 has low power pre-lasing output during the ramp down. The delay time t1 is approximately 10 ms.

At time t1, ET 302 stays at 1; GS 311 starts to generate TTL pulse train 312 with a constant pulse width (in the range of 4-10 microseconds) and pulse repetition rate 1/f, FPC 322 ramps from 0 to 1. This ramp up time can be a few times of 1/f, predetermined through a microprocessor and a circuit of the first pulse controller 61. A typical ramp up time is approximately 3 ms. The RF driver 64 mixes GS 311-312 and FPC 322-323 to produce a modulated RF power of RFP 332a-332b, which has the same pulse width and frequency of GS 311-312 but a ramp-up envelope 333 defined by FPC 322-323. As a result, the laser 21 starts to produce pulses 341a during the ramp-up 333. At the end of the ramp-up process 333, normal laser pulses 341b are produced. The first pulse 341a has amplitude not as high as the normal laser pulse 341b. The number of low-amplitude pulses 341a depends on a predetermined rise time of FPC 322.

FIG. 4 illustrates schematically first pulse suppression through pre-lasing and pump current ramping. FIG. 4a) shows temporal profile of external trigger signal ET, 4b) gate signal GS, 4c) first pulse control signal FPC, 4d) RF power RFP and 4f) laser pulse LP. FIG. 4e) shows diode laser pump current C with a ramping profile. In this embodiment, both the RF power RFP and diode laser pump current C are modulated. During previous laser-ready mode, the ET 400 equals to 0, GS 410 equals to 0, FPC 420 equals to 1, RFP 430 equals to 100%, C 450 equals to level B and LP 430 equals to 0. Level B of diode laser pump current C is usually about 60%+/−20% of the normal operation current A. LP 430 equals to 0 indicating no laser pulse output.

At time 0 laser is switched from laser-ready mode to pulse-on mode, the input signal ET 401 of the first pulse controller 61 changes from 0 to 1. As a response, the first pulse controller 61 sends a ramp-down signal 421 to RF driver 64 and sends a delayed signal at time t1 to the gate signal generator 62 that starts a gate signal 411. The RFP 431 to the Q-switch 80 follows the ramp-down curve of FPC 421. The purpose of this ramp-down process is to deplete energy stored inside medium during the laser-ready mode. The LP 440 has low power pre-lasing output during the ramp down. The delay time t1 is approximately 10 ms.

At time t1, ET 402 stays at 1; GS 411 starts to generate TTL pulse train 412 with a constant pulse width (4-10 microseconds) and pulse repetition rate 1/f. However, FPC 422 jumps up from 0 to 1. The RF driver 64 mixes GS 411-412 and FPC 422-423 to produce a modulated RF power of RFP 432-433, which has the same pulse width and frequency of GS 411-412 but an envelope 433 defined by FPC 423. The diode laser pump current C 451 starts to ramp up from level B at time t1 to level A at time t2. Since the first pulse controller 61 also connects to the diode laser pump controller (not shown), this ramp up in pump current C can be synchronized to FPC 422. As a result, the laser 21 starts to produce pulses 441a during the ramp-up 451. At the end of the ramp-up process 452, normal laser pulses 441b are produced. The first pulse 441a has amplitude not as high as the normal laser pulse 441b. The number of low-amplitude pulses 441a depends on a predetermined rise time of the pump current C 451.

FIG. 5 illustrates schematically first pulse suppression through pre-lasing and gate width ramping. FIG. 5a) shows temporal profile of external trigger signal ET, 5b) gate signal GS, 5c) first pulse control signal FPC, 5d) RF power RFP and 5e) laser pulse LP. Here the diode pump current C (not shown) is kept constant. During previous laser-ready mode, the ET 500 equals to 0, GS 510 equals to 0, FPC 520 equals to 1, RFP 530 equals to 100% and LP 540 equals to 0. LP 540 equals to 0 indicating no laser pulse output.

At time 0 laser is switched from laser-ready mode to pulse-on mode, the input signal ET 501 of the first pulse controller 61 changes from 0 to 1. As a response, the first pulse controller 61 sends a ramp-down signal 521 to RF driver 64 and sends a delayed signal at time t1 to the gate signal generator 62 that starts a gate signal 511. The RFP 531 to the Q-switch 80 follows the ramp-down curve of FPC 521. The purpose of this ramp-down process is to deplete energy stored inside medium during the laser-ready mode. The LP 540 has low power pre-lasing output during the ramp down. The delay time t1 is approximately 10 ms.

At time t1, ET 502 stays at 1; GS 511 starts to generate TTL pulse train 512 with a constant pulse repetition rate 1/F. However, the gate width has a ramp up profile, as shown in FIG. 5b). FPC 522 jumps up from 0 to 1. The ramp up time is typically a few times of 1/f, predetermined through a microprocessor and a circuit of the first pulse controller 61. The RF driver 64 mixes GS 511-514 and FPC 522-523 to produce a modulated RF power of RFP 532-535, which has a pulse width modulation defined by the gate width ramp up profile of GS 511-514. Narrowed gate pulse 512 does not provide sufficient time for a pulse to fully develop. As a result, the laser 21 starts to produce pulses 541 during the ramp-up 533-535. At the end of the ramp-up process 533, normal laser pulses 543 are produced. The first pulse 541 has amplitude not as high as the normal laser pulse 543. The number of low-amplitude pulses depends on a predetermined ramp up time of gate pulses 512-514.

Although the above description is based on preferred embodiments to illustrate the present invention, various modifications can be made without departing from the scopes of the appended claims.

What is claimed is:

1. A laser system comprising:
   a resonant cavity that defines an optical path within which electromagnetic radiation is processed prior to being emitted from the laser system; and
   a Q-switch disposed along the optical path defined by the resonant cavity, the Q-switch being configured such that a mode of operation of the Q-switch is based on a trigger signal,
   wherein a first mode of operation of the Q-switch comprises a laser-ready mode during which an optical transmittance of the Q-switch is maintained at or near the lowest optical transmittance attainable by the Q-switch,
   wherein a second mode of operation of the Q-switch comprises a pulse-on mode during which the optical transmittance of the Q-switch is modulated with a predetermined frequency and amplitude, and
   wherein in response to an indication in the trigger signal for the mode of operation of the Q-switch to change from laser-ready mode to pulse-on mode, the Q-switch operates such that before the Q-switch commences operating in the pulse-on mode of operation, the optical transmittance of the Q-switch ramps up gradually from the optical transmittance of the Q-switch during the laser-ready mode to an optical transmittance substantially larger than the optical transmittance of the Q-switch during the laser-ready mode.

2. The laser system of claim 1, wherein the optical transmittance substantially larger than the optical transmittance of the Q-switch during the laser-ready mode is a maximum optical transmittance of the Q-switch.

3. The laser system of claim 1, wherein as the Q-switch commences operating in the pulse-on mode, the amplitude of the optical transmittance of the Q-switch is incrementally increased between successive modulations until the amplitude reaches the predetermined amplitude for the modulations.

4. The laser system of claim 3, wherein the modulation of the optical transmittance of the Q-switch during pulse-on mode causes the laser system to emit pulses of electromagnetic radiation, and wherein incrementally increasing the optical transmittance of the Q-switch between successive modulations as the Q-switch commences operating in the pulse-on mode causes the intensity of successive pulses of electromagnetic radiation emitted by the laser system to increase incrementally.

5. The laser system of claim 1, wherein the Q-switch is an RF Q-switch.

6. The laser system of claim 1, wherein the trigger signal is input to the laser system based on operator inputs.

7. The laser system of claim 1, wherein the laser system is configured to provide electromagnetic radiation for the ablation of soft tissue.

8. A laser system comprising:
   a gain medium;
   a pump source that provides stimulation energy to the gain medium that causes the gain medium to emit electromagnetic radiation; and
   a Q-switch disposed within an optical path along which electromagnetic radiation emitted by the gain medium is directed,
   wherein a first mode of operation of the Q-switch comprises a laser-ready mode during which an optical transmittance of the Q-switch is maintained at or near the lowest optical transmittance attainable by the Q-switch,
   wherein a second mode of operation of the Q-switch comprises a pulse-on mode during which the optical transmittance of the Q-switch is modulated with a predetermined frequency and amplitude, and
   wherein in response to an indication in the trigger signal for the mode of operation of the Q-switch to change from laser-ready mode to pulse-on mode, the Q-switch operates such that before the Q-switch commences operating in the pulse-on mode of operation, the optical transmittance of the Q-switch ramps up gradually from the optical transmittance of the Q-switch during the laser-ready mode to an optical transmittance substantially larger than the optical transmittance of the Q-switch during the laser-ready mode.

9. The laser system of claim 8, wherein the optical transmittance substantially larger than the optical transmittance of the Q-switch during the laser-ready mode is a maximum optical transmittance of the Q-switch.

10. The laser system of claim 8, wherein if the Q-switch is operating in the laser-ready mode, the pump source provides a first, relatively low, level of energy to the gain medium, and wherein if the Q-switch is operating in the pulse-on mode, the pump source provides a second level of energy to the gain medium that is higher than the first level of energy.

11. The laser system of claim 10, wherein as the Q-switch commences operating in the pulse-on mode, the level of energy provided to the gain medium by the pump source is gradually increased from the first level of energy.

12. The laser system of claim 11, wherein the level of energy provided to the gain medium by the pump source is gradually increased from the first level of energy to the second level of energy.

13. The laser system of claim 11, wherein the modulation of the optical transmittance of the Q-switch during pulse-on mode causes the laser system to emit pulses of electromagnetic radiation, and wherein gradually increasing the level of energy provided to the gain medium by the pump source from the first level of energy as the Q-switch commences operation in the pulse-on mode causes the intensity of successive pulses of electromagnetic radiation emitted by the laser system to increase gradually.

14. The laser system of claim 8, wherein the Q-switch is an RF Q-switch.

15. The laser system of claim 8, wherein the trigger signal is input to the laser system based on operator inputs.

16. The laser system of claim 8, wherein the laser system is configured to provide electromagnetic radiation for the ablation of soft tissue.

* * * * *